United States Patent
Dijkman

(10) Patent No.: US 11,401,537 B2
(45) Date of Patent: Aug. 2, 2022

(54) PROCESS FOR PRODUCING POLYHYDROXYALKANOATE

(71) Applicant: Paques I.P. B.V., Balk (NL)

(72) Inventor: Hendrik Dijkman, Balk (NL)

(73) Assignee: PAQUES BIOMATERIALS HOLDING B.V., Balk (NL)

( * ) Notice: Subject to any disclaimer, the term of this patent is extended or adjusted under 35 U.S.C. 154(b) by 712 days.

(21) Appl. No.: 15/780,407

(22) PCT Filed: Dec. 2, 2016

(86) PCT No.: PCT/EP2016/079633
§ 371 (c)(1),
(2) Date: May 31, 2018

(87) PCT Pub. No.: WO2017/093509
PCT Pub. Date: Jun. 8, 2017

(65) Prior Publication Data
US 2018/0363013 A1 Dec. 20, 2018

(30) Foreign Application Priority Data
Dec. 3, 2015 (EP) .................................... 15197866

(51) Int. Cl.
| | | |
|---|---|---|
| C12P 7/625 | (2022.01) | |
| C02F 3/00 | (2006.01) | |
| C02F 3/30 | (2006.01) | |
| C02F 3/34 | (2006.01) | |
| C02F 3/12 | (2006.01) | |

(52) U.S. Cl.
CPC .............. *C12P 7/625* (2013.01); *C02F 3/006* (2013.01); *C02F 3/1263* (2013.01); *C02F 3/30* (2013.01); *C02F 3/34* (2013.01); *C02F 3/348* (2013.01); *C02F 2203/004* (2013.01); *C02F 2209/16* (2013.01); *C02F 2209/18* (2013.01); *C02F 2209/22* (2013.01); *C02F 2305/06* (2013.01); *Y02W 10/10* (2015.05)

(58) Field of Classification Search
CPC ............ C12P 7/625; C02F 3/12; Y02W 10/10
See application file for complete search history.

(56) References Cited

U.S. PATENT DOCUMENTS

2009/0317879 A1 12/2009 Criddle et al.
2014/0242641 A1 8/2014 Tamis et al.

FOREIGN PATENT DOCUMENTS

| WO | WO-00/52189 A1 | 9/2000 |
|---|---|---|
| WO | WO-2011/073744 A1 | 6/2011 |
| WO | WO-2012/023114 A1 | 2/2012 |
| WO | WO-2013/022874 A1 | 2/2013 |
| WO | WO-2014/108864 A1 | 7/2014 |
| WO | WO-2014/108878 A1 | 7/2014 |

OTHER PUBLICATIONS

Johnson ("Influence of the C/N ratio on the performance of polyhydroxybutyrate (PHB) producing sequencing batch reactors at short SRTs" Water Research, 44, 2010, 2141-2152). (Year: 2010).*
Tamis ("Enrichment of Plasticicumulans acidivorans at pilot-scale for PHA production on industrial wastewater" Journal of Biotechnology, 192 (2014), 161-169). (Year: 2014).*
International Search Report issued in International Patent Application No. PCT/EP2016/079633, dated Mar. 7, 2017.
Bengtsson et al., "Production of polyhydroxyalkanoates by activated sludge treating a paper mill wastewater", Bioresource Technology, 2008, vol. 99, pp. 509-516.
Serafim et al., "Strategies for PHA production by mixed cultures and renewable waste materials", Appl. Microbiol Biotechnol, 2008, vol. 81, pp. 615-628.

* cited by examiner

*Primary Examiner* — Robert J Yamasaki
*Assistant Examiner* — Charles Zoltan Constantine
(74) *Attorney, Agent, or Firm* — Foley & Lardner LLP

(57) ABSTRACT

High levels of polyhydroxyalkanoates (PHA) can be produced from wastewater comprising Readily Biodegradable COD (RBCOD) using activated sludge comprising microorganisms capable of accumulating PHA by contacting the wastewater with the activated sludge in the presence of dissolved oxygen during a first period of time, to obtain PHA-loaded activated sludge, and then supplying elements essential for growth such as nitrogen and phosphorus and allowing up-take of these elements and limited growth during a second period of time, the supplied amount of at least of one of said essential elements compared to the amount of RBCOD supplied in step a) limiting the growth to an extent that not all PHA is used for growth, to obtain grown activated sludge; and removing or harvesting part of the PHA-loaded activated sludge and/or part of the grown activated sludge, so that the total average retention time of the sludge is less than 72 h.

20 Claims, 4 Drawing Sheets

PROCESS FOR PRODUCING POLYHYDROXYALKANOATE

CROSS-REFERENCE TO RELATED APPLICATIONS

This application is the National Phase of International Patent Application No. PCT/EP2016/079633, filed Dec. 2, 2016, published on Jun. 8, 2017 as WO 2017/093509 A1, which claims priority to European Patent Application No. 15197866.5, filed Dec. 3, 2015. The contents of these applications are herein incorporated by reference in their entirety.

FIELD OF THE INVENTION

The invention relates to a process for producing a microbial storage compound (MSC), in particular a process for producing polyhydroxyalkanoate (PHA) using micro-organisms accumulating the microbial storage compound.

BACKGROUND

It is known that some micro-organisms that are found in sludge used for aerobic wastewater treatment are able to produce microbial storage compounds, such as for example poly(hydroxyalkanoate) (PHA) or glycogen, as a reserve compound. There is increasing interest in wastewater treatment processes wherein the accumulation of PHA in PHA-accumulating bacteria is maximised in order to recover such PHA from these bacteria, for example for application as bioplastics.

Processes for the selection of micro-organisms capable of producing PHA or other microbial storage compounds are known in the art and typically comprise several cycles alternating a so-called feast phase wherein sludge comprising PHA-accumulating bacteria is fed with a substrate that comprises readily biodegradable organic compounds (so-called readily biodegradable chemical oxygen demand or RBCOD) with a so-called famine phase wherein substrate is withheld from the bacteria. In the feast phase, the PHA-accumulating bacteria are converting RBCOD such as volatile fatty acids (VFA) into PHA. In the famine phase, the PHA accumulated in the bacteria is used as feed, resulting in selection of those bacteria that are capable of accumulating PHA or other bacterial storage compounds.

For example, WO00/52189 discloses a process for the production of polyhydroxy-alkanoate wherein in a first step microorganisms capable of accumulating PHA are selected by alternatingly subjecting the micro-organisms to a phase wherein substrate is added (feast phase) and a phase wherein substrate is withheld (famine phase). In an accumulation step, PHA is accumulated by subjecting some of the micro-organisms selected in the first step to a substrate, preferably a fatty acid-comprising stream. In the process of WO00/52189, the selection step with alternating feast and famine phases is carried out in a first reactor and the accumulation step is carried out in a separate second reactor.

WO2011/073744 also discloses a process for selecting filamentous micro-organisms (biomass) capable of producing PHA by alternatingly subjecting biomass to feast and famine conditions. In the process of WO2011/073744, the feast and famine conditions may be applied sequentially in the same reactor, or in separate reactors. Sludge (biomass) withdrawn from the selection process may be subjected to further accumulation in a separate step or to extraction of PHA.

WO2012/023114, WO2014/108864 and WO2014/108878 describe similar methods. In all these methods, any accumulation step is performed in a separate reactor. In the process of WO2014/108878, the nitrogen to RBCOD and/or phosphorus to RBCOD ratios in the feed are controlled.

WO2013/022874 discloses a process for PHA production using return sludge in an aeration basin in such a manner that a famine-feast regime is provided in the same aeration basin. The return sludge may be treated in a return stream reactor in which a relatively low feed-to-biomass ratio is applied. No accumulation is disclosed or suggested.

Serafim et al. *Appl. Microbiol. Biotechnol.* 81 (2008) 615-628, and Bengtsson et al. *Bioresource Technology* 99 (2008) 509-516, disclose processes for the production of PHA using mixed cultures in sequencing batch or continuous reactors, wherein the feast and famine cycles may be performed in a single (selection) reactor. In the prior art methods, the selection for PHA-accumulating organisms is performed using a feast and famine regime and an excess of nutrients with the purpose of growing biomass enriched in organisms capable of PHA accumulation. The final accumulation of PHA in the obtained enriched biomass is to be carried out in a separate accumulation step in order to reach maximum PHA content in the sludge.

US 2009/0317879 discloses a method of PHA biosynthesis, by alternating phases of nutrient deprivation (feast) and carbon feedstock deprivation (famine) of PHA-producing microbes. However, the PHA content of the microbes grown according to US '879 appears to be rather low ("typically above 20%") and carbon supply and nutrient supply are controlled in an absolute way: nutrients are absent in the first cycling stage and carbon source is absent in the second cycling stage. This implies complete separation of accumulation stages and growth stages and precludes continuous operation. Any further guidance on how to control carbon and nutrient supply and retention times in order to arrive to arrive at useful levels of PHA and efficient and simplified process management is lacking in US '879.

SUMMARY OF THE INVENTION

It has now been found that the process for selection of micro-organisms capable of producing microbial storage compounds (MSC) and further accumulation of such MSC in selected micro-organisms can be improved and integrated. Through control of levels and providing periods of enhanced presence and decreased presence of elements essential for growth and management of the sludge retention time, high PHA levels up to 80 wt. % or higher based on organic content of the sludge can be reached already in the selection process without the requirement of an additional accumulation step.

Besides a simplification of the overall process for PHA production from wastewater containing RBCOD by removing the accumulation step, also the selection is improved on two points. First of all, the new procedure selects for PHA-accumulating organisms that can reach a very high intercellular PHA content, whereas the prior art selection procedures select for fast RBCOD up-take but not necessarily for the capacity of reaching highest PHA levels after accumulation. Secondly, the limited presence of RBCOD and nutrients at the same time in combination with the short sludge retention times applied minimises the presence of other non PHA accumulating organisms in the produced biomass. This results in a higher overall PHA content in the sludge produced which increases the yield of PHA on RBCOD and reduces cost for purification of the PHA.

DESCRIPTION OF THE INVENTION

Figure 1:
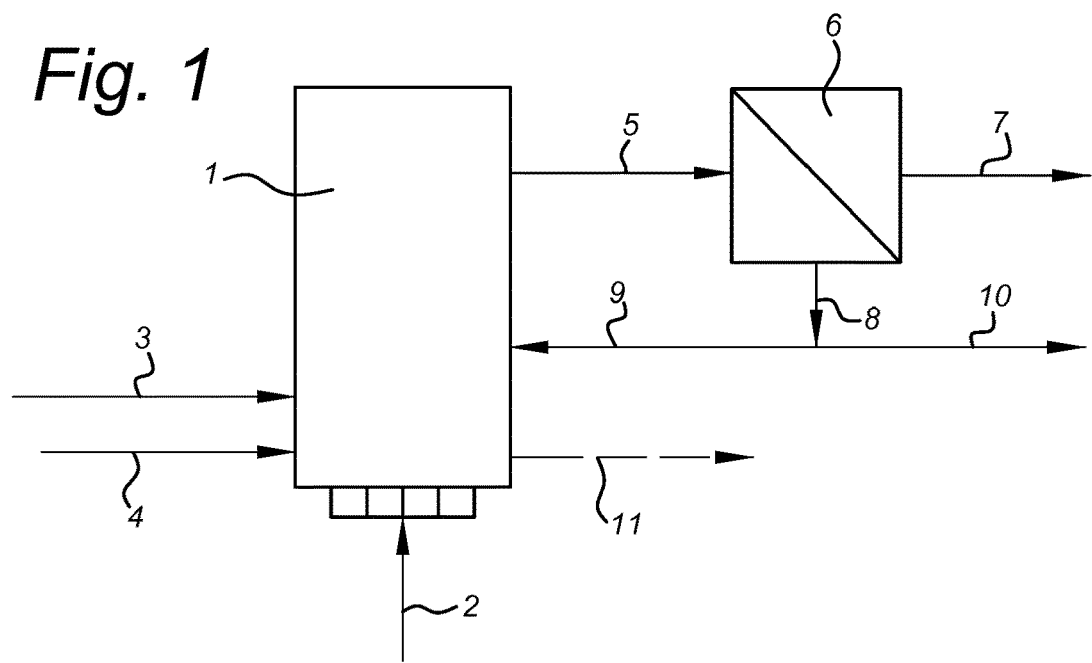
FIGS. 1 and 2 schematically show a one-reactor system and a two-reactor system, respectively, for carrying out the process of the invention.

The process according to the invention is a process for producing a microbial storage compound (MSC), in particular a polyhydroxyalkanoate (PHA). In the process, a stream of wastewater that comprises organic compounds including readily biodegradable chemical oxygen demand (RBCOD) and possibly also other (=less readily) biodegradable chemical oxygen demand (OBCOD) is supplied to a reactor containing activated sludge comprising micro-organisms capable of accumulating the desired microbial storage compound. The process is carried out in one or more reactors, in particular in a single reactor or in two consecutive reactors.

More in particular, the present process comprises the following steps:

a) supplying a stream of the wastewater to a first reactor stage in a first reactor (which may be the only reactor), and contacting the wastewater with the activated sludge under MSC-accumulating conditions during a first period of time, the MSC-accumulating conditions comprising the presence of dissolved oxygen, to obtain MSC-loaded activated sludge comprising MSC and treated wastewater;

b) providing that at least part of the MSC-loaded activated sludge and at least part of the treated wastewater obtained in the first reactor stage, i.e. in step a), becomes present in a second reactor stage in the first (same) reactor or in a second reactor;

c) supplying elements essential for growth to the second reactor stage and contacting the wastewater with the activated sludge under growth conditions during a second period of time, the growth conditions comprising the presence of dissolved oxygen, wherein the supplied amount of at least one of said essential elements compared to the amount of RBCOD supplied in step a) limits the growth to an extent that not all MSC is used for growth, to obtain grown activated sludge comprising residual MSC;

d) providing that at least part of the grown activated sludge produced in the second reactor stage i.e. in step c), becomes present in the first reactor stage;

e) removing part of the treated wastewater from the first reactor stage, i.e. from the first reactor, during or after step a) and/or from the second reactor stage, i.e. from the first or second reactor, during or after step c) and removing part of the MSC-loaded activated sludge during or after step a) and/or part of the grown activated sludge during or after step c), the activated sludge removed during or after step a) or during or after step c) comprising MSC at a level of at least 50 wt. %, preferably at least 60 wt. %, based on dry weight of the organic part of the sludge, and the parts being such that the average retention time of the activated sludge (SRT) in the first and optional second reactor together is less than 72 h.

Since the present process is a cyclic process, step d) or e) is followed by step a) etc.

In the context of the present invention the following definitions are applied:

"Microbial storage compounds" are compounds produced by microorganisms such as bacteria, archaea, moulds, and algae, for storing their surplus energy. The compounds include esters, polyesters, polythioesters, triglycerides, other fats and oils, and polysaccharides such as glycogen. Polyesters resulting from intermolecular esterification of hydroxy-carboxylic acids are an important class of microbial storage compounds, the most prominent ones being poly-hydroxyalkanoic esters, in particular poly-β-hydroxyalkanoic esters, such as poly-β-hydroxybutyrate (PHB) and poly-β-hydroxyvalerate (PHV) having the formulae below, wherein n may range from tens to hundreds or even many thousands, as well as their copolymers.

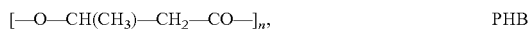

$$[-O-CH(CH_3)-CH_2-CO-]_n, \quad PHB$$

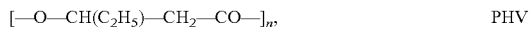

$$[-O-CH(C_2H_5)-CH_2-CO-]_n, \quad PHV$$

The poly-hydroxyalkanoic esters (or poly-oxyalkanoates) are commonly (and herein) referred to as polyhydroxyalkanoate (PHA). Herein below, the MSC are typically exemplified by PHA, but what applies to PHA, will apply to other MSC as well.

"Chemical oxygen Demand" (COD) refers to organic material that can be oxidised to smaller molecules, ultimately to carbon dioxide and water, and the term expresses the amount of oxygen that would be needed to oxidise the organic material in a litre of wastewater.

"Biodegradable COD" refers to organic material in wastewater that can be assimilated for biomass growth.

"Substrate" means substrate for assimilation by microorganisms to allow them to grow, i.e. equivalent to Biodegradable COD.

"Readily Biodegradable Chemical Oxygen Demand (RBCOD)" refers to relatively small organic molecules that can be quickly assimilated by microorganisms as further illustrated below".

"Other Biodegradable Chemical Oxygen Demand (OBCOD)" refers to bio-degradable COD other than RBCOD, i.e. more complex and less accessible organic compounds, for example complex polysaccharides, fats and proteins, as well as organic compounds having relatively few oxygen-containing groups and relatively large hydrocarbon groups, such as long-chain fatty acids.

"Wastewater" refers to an aqueous stream comprising COD that needs to be treated before it can be reused or discharged to the environment. Wastewater for example includes process water, side-product or intermediate product streams from bio-based or other industries, as further illustrated below.

"Sludge" refers to any solid or solid-like material present in a reactor or its influent or effluent which can be separated from the liquid part of the reactor (or influent or effluent) by physical means, such as filters, cyclones, settlers, membranes and the like. The sludge can comprise an organic part, which includes all biological material as well as non-soluble or not finely dispersible organic compounds, and an inorganic part, which includes non-soluble or not finely dispersible salts and other inorganic material. Thus, "dry organic sludge" comprises solid material, from which inorganic materials (salts, ash) and water and other liquids have been separated or have been taken into account in calculating product levels.

"Reactor stage" relates to a reactor content entity which is separated from another reactor content entity in space or time. For example, it can be a compartment of a reactor which is physically partly or wholly separated (by a wall, a narrowing or another barrier) from another part of the reactor. It can also be a separate reactor. Further, a reactor stage may be a reactor thereof which has a different content, composition or set of conditions from another stage, in the same space, which follows or precedes the reactor stage (in a non-continuous process).

"MSC-accumulating conditions" (in particular PHA-accumulating conditions) refer to conditions allowing accumulation of MSC (PHA) in the bacterial sludge, also commonly referred to as feast conditions. These comprise the presence of substrate in the form of RBCOD and the presence of dissolved oxygen. Dissolved oxygen means dissolved molecular oxygen unless stated otherwise. Preferably, the dissolved oxygen concentration is at least 0.32 mg, more preferably at least 0.5 mg $O_2$ per litre. The MSC-accumulating conditions preferably further comprise a pH in the range of from 4 to 10, more preferably of from 6 to 8, a temperature in the range of from 10 to 50° C., more preferably of from 20 to 40° C., and a conductivity in the range of from 0 to 20 mS/cm. It is to be noted that MSC-accumulating conditions as used herein imply relative promotion of accumulation of MSC (PHA) but do not exclude growth.

"Growth conditions" refer to conditions allowing growth, i.e. increase of the population, of bacterial sludge, including MSC-accumulating (PHA-accumulating) micro-organisms, also sometimes referred to as famine conditions. These comprise the presence of elements essential for growth as further defined herein and allow uptake of the elements by the sludge. The growth conditions further comprise the presence of dissolved oxygen, preferably at least 0.32 mg, more preferably at least 0.5 mg $O_2$ per litre, and preferably comprise a pH in the range of from 4 to 10, more preferably of from 6 to 8, a temperature in the range of from 10 to 50° C., more preferably of from 20 to 40° C., and a conductivity in the range of from 0 to 20 mS/cm. It is to be noted that growth conditions as used herein imply a relative promotion of microbial growth but do not exclude accumulation and preferably avoid full breakdown of MSC (PHA). In particular, "accumulating conditions" and "growth conditions" may differ essentially only in the ratio of RBCOD supply to supply of elements essential for growth.

"Elements essential for growth" or "nutrients essential for growth" comprise the commonly known elements—other than carbon, oxygen and hydrogen—, which the cell requires for proper growth. These include macro-elements N, P, K and S, micro-elements Mg, Ca, Fe, and trace elements such as Mn, Mo, Zn, Co, Cu, Ni, B, Se, W, Cr, as well as vitamins. While any of the elements, including vitamins, can be used for controlling the growth of organisms, nitrogen and phosphorus can be advantageously used. The elements essential for growth can be provided in any conventional and appropriate, preferably water-soluble, form, e.g. as ammonium salts or urea, phosphate salts, potassium, magnesium, calcium or iron salts (chloride, nitrate, acetate, etc.), sulfate salts, trace metal salts, vitamins or vitamin salts, etc.

"Sludge Retention Time" (SRT) is the average retention time of total sludge in the reactor system of the present process. It can be different from the Hydraulic (liquid) Retention Time (HRT) by partial separation and return of sludge. For this purpose SRT is defined as the sum of the time-averaged amount of sludge present in the first and optional second reactor together (kg dry solids) divided by the time-averaged amount of solids produced in the system and removed from the system (kg dry solids/h).

An important feature of the present process is a control of accumulation conditions and growth conditions for the MSC-producing sludge. In step a), accumulation conditions prevail over growth conditions. This can be achieved by providing that the relative level of elements essential for growth is low compared to the supply of RBCOD, i.e. carbon-containing feed. Step c) allows uptake of elements essential for growth by the sludge and growth may be more predominant than in step a), but well below the extent where all MSC would be used for growth.

The limiting amount of the one or more essential elements to be supplied in step c) of the present process, is such that the microorganisms can grow, for which growth the accumulated MSC will at least partly provide the carbon, hydrogen and oxygen source, but the growth should not result in all MSC being consumed. The amount of essential elements to be supplied which ensures that not all MSC is used for growth depends on the particular element which is limiting. If the limiting element comprises nitrogen, the amount of nitrogen supplied in step c) together with dissolved nitrogen supplied with the wastewater in step a), divided by the amount of RBCOD-carbon supplied in step a) ($N_c/C_a$) is preferably between 1/12 and 1/100. If the limiting element comprises phosphorus, the amount of phosphorus divided by the amount of RBCOD-carbon supplied in step a) ($P_c/C_a$) is below tween 1/60 and 1/500. For other essential elements, corresponding values can be calculated as described below. In these calculations, the elements are taken on elemental basis, although they will usually be provided in compound (salt or other) form.

More preferably, the ratio $N_c/C_a$ is below 1/15, even more preferably below 1/20, down to 1/75. Alternatively, $P_c/C_a$ is more preferably below 1/75, even more preferably below 1/100, preferably down to 1/375.

If the limiting element comprises another element, the level thereof can be determined by the skilled person, on the basis of the known composition and elemental needs of bacteria. For example, the limiting level of phosphorus can be taken as 5 times lower than the limiting level for nitrogen and the limiting levels of sulfur, potassium, calcium, magnesium, iron and trace metals such as Cu, can be taken at 10 times (S, K), 30 times (Ca, Mg), 50 times (Fe), and 300 times (trace metals), respectively, lower than the nitrogen level. The skilled person will be able to determine the limiting levels of these and other elements and vitamins, should he choose one of these for ensuring limited growth, by suitable routine experimentation involving varying levels of the element or vitamin in question. Essential elements which are not used at a growth-limiting level, are often already present in the wastewater in sufficient amounts or can be supplied if necessary, to achieve non-limiting levels. Common and commercially available element mixtures contain the various elements at the required relative levels.

It is preferred that the level of at least one of the elements for growth, such as N or P, in the wastewater is limiting compared to the level of RBCOD. Advantageously, the wastewater as supplied in step a) has a weight ratio of nitrogen amount to amount of RBCOD-carbon ($N_a/C_a$) below 1/15 and/or a weight ratio of phosphorus amount to amount of RBCOD-carbon ($P_a/C_a$) below 1/75. More preferably, $N_a/C_a$ is below 1/20, even more preferably below 1/25, down to very low levels, e.g. 1/1000, preferably down to 1/500. Alternatively, $P_a/C_a$ is preferably below 1/100, more preferably below 1/125, down to e.g. 1/5000, preferably down to 1/2500. If the raw wastewater has nitrogen and/or phosphorus to RBCOD levels exceeding these ratios, the N/C or P/C levels can be reduced to the preferred levels by inserting a pre-treatment step aiming at lowering the weight ratio of relevant elements to the amount of RBCOD, by partially removing said one or more elements essential for growth, in particular N or P. For example, phosphate (P) and ammonia (N) can be removed by addition of magnesium to the wastewater and removing precipitated struvite (ammonium magnesium phosphate) from the wastewater prior to step a). Alternatively, or additionally, the ratio can be lowered by adding RBCOD.

Table 1 below gives more guidance on the achievable PHA content as a function of $N_c/C_a$ or $P_c/C_a$.

TABLE 1

PHA content vs. nitrogen and phosphorus

| % PHA | $N_c/C_a$ | $P_c/C_a$ |
|---|---|---|
| 94 | 1/112 | 1/558 |
| 93 | 1/96 | 1/481 |
| 92 | 1/85 | 1/424 |
| 91 | 1/76 | 1/378 |
| 90 | 1/68 | 1/339 |
| 88 | 1/56 | 1/278 |
| 85 | 1/46 | 1/229 |
| 80 | 1/35 | 1/174 |
| 75 | 1/28 | 1/142 |
| 70 | 1/24 | 1/119 |
| 65 | 1/21 | 1/104 |
| 60 | 1/18 | 1/92 |
| 55 | 1/17 | 1/83 |
| 50 | 1/15 | 1/75 |
| 40 | 1/13 | 1/64 |
| 30 | 1/11 | 1/57 |
| 20 | 1/10 | 1/51 |
| 10 | 1/9 | 1/46 |

The desired level of nutrients (nitrogen, phosphorus or other) or the desired ratios of nutrient to carbon can be achieved by assaying the level of the nutrient and, if necessary, of carbon, in the wastewater on-line or off-line, using conventionally known methods, including colorimetric methods, chromatographic methods, element-specific electrodes, titration, Kjeldahl (nitrogen) etc., and then adding one or more nutrients or carbon (RBCOD) as appropriate.

As defined above, RBCOD refers to relatively simple organic molecules that can be assimilated for growth of micro-organisms and can be quickly taken up and converted to a storage compound, often without requiring hydrolysis. Examples of such RBCOD include volatile fatty acids, also referred to as short-chain fatty acids, i.e. having up to 6 carbon atoms, such as formic acid, acetic acid, propionic acid, butyric acid, isobutyric acid, valeric acid, isovaleric acid, and caproic acid, hydroxy acids such as lactic acid, carbohydrates such as monosaccharides and disaccharides, uronic acids, alcohols, ketones, and aldehydes, preferably alcohols, ketones, and aldehydes with up to six carbon atoms and combinations of two or more thereof. In other words, RBCOD includes organic compounds having up to 6 carbon atoms per molecule and having at least one hydroxylic (C—OH) or ketonic (C=O) oxygen atom per molecule and at least one oxygen atom per four carbon atoms, preferably having carbon, hydrogen and oxygen atoms only, as well as disaccharides. The concentration of RBCOD can be determined by means of standardised methods of respirometry that determine the fraction of wastewater COD that is rapidly utilised when an aliquot of wastewater with a specified amount of biomass is pulse-fed with substrate under controlled conditions. An example of a suitable standardised method of respirometry is disclosed in M. Henze et al., *Activated Sludge Models ASM1, ASM2, ASM2d and ASM3*, IWA Publishing, London, 2000, p. 16-17; ISBN 1900222248.

The wastewater stream may be any wastewater stream that comprises RBCOD. The stream may be municipal, industrial or agricultural wastewater or process streams or residual streams from solid biodegradable waste as such or it may be municipal, industrial or agricultural wastewater that has been pre-treated, for example has been pre-hydrolysed to convert so-called OBCOD to RBCOD, and/or that has been pre-acidified or fermented to convert saccharides or other compounds to carboxylic acids, preferably volatile fatty acids, lactic acid or ethanol.

The wastewater typically contains more than 50 mg, preferably more than 100 mg RBCOD per l. More preferably, the wastewater comprises RBCOD in the range of from 0.5 to 50 grams per litre, more preferably in the range of from 1 to 20 grams per litre. It preferably comprises volatile ($C_1$-$C_6$) fatty acids and/or lactic acid and/or ethanol, more preferably in the range of from 0.5 to 50 grams per litre volatile fatty acids, even more preferably in the range of from 1 to 20 grams per litre.

The wastewater supplied to the first reactor stage in step a) may further comprise OBCOD. Preferably, it contains more RBCOD than OBCOD. An advantage of the present process involving short cycle times between the two reaction stages, separation in time or place of the availability of RBCOD and nutrients and the relatively short SRT, is that the microbial population is highly selective for MSC production from RBCOD, and other bacterial populations are suppressed so that it is relatively insensitive to OBCOD digestion and results in high MSC yields. If the level of OBCOD is more than 0.2 times the level of RBCOD, it is preferred to carry out the present process in two reactors. In such an arrangement it is advantageous to separate the treated wastewater from the sludge before the concentrated sludge is transferred from the first to the second reactor. This limits the amount of treated wastewater containing OBCOD to the second reactor and additionally prevents conversion of OBCOD and the resulting growth of undesired microorganisms. When the wastewater contains high levels of OBCOD, a post-treatment for degrading OBCOD may be desirable.

Preferably, the microbial storage compound is glycogen or PHA, more preferably PHA, and the process is a process for producing PHA. In that case, the activated sludge comprises PHA-accumulating micro-organisms, preferably PHA-accumulating bacteria. Once the process operates in steady state, the activated sludge is the activated sludge that is further enriched in accumulating micro-organisms obtained in steps a) and c). At the start of the process, the first reactor stage may be inoculated with activated sludge or other samples comprising such accumulating micro-organisms or with strains of micro-organisms capable of accumulating the desired microbial storage compound, in particular PHA. The stream of wastewater supplied to the first reactor often comprises micro-organisms capable of accumulating the desired microbial storage compound, and then the process may be started without inoculating with sludge or with such micro-organisms.

PHA-accumulating bacteria and archaea as well as other micro-organisms capable of accumulating microbial storage compounds are typically present in non-axenic cultures of micro-organisms such as are found in soil, natural water or mixed biomass samples. They can also be isolated or enriched from common municipal wastewater plants. The PHA-accumulating bacteria can belong to various genera such as *Alcaligenes* (e.g. *A. latus*), *Ralstonia* (e.g. *R. eutropha*), *Cupriavidus* (e.g. *C. necator*), *Chromatium* (e.g. *C. vinosum*) *Mycobacterium, Bacillus, Pseudo-monas, Thauera*, etc. They may specifically or non-specifically grow on various carbon sources such as glucose, methanol, ethanol, acetate and/or other fatty acids. See e.g. Tan G-Y. A. et al. *Polymers* 2014, 6, 706-754; Huang Y-T. et al. *J. Microbiol. Biotechnol.* 2012, 22, 1141-47. Particularly useful are bacteria of the genus *Plasticicumulans*, such as *P. acidivorans* (acetate-consuming) and *P. lacatativorans* (lactate-consuming), see e.g. Jiang et al. *Int. J. systematic Evolutionary Microbiology* 2011, 61, 2314-2319, Tamis et al. *J. Biotechnology* 2014, 192, 161-169. Advantageously, the micro-organisms used in the present process comprise bacteria of the genus *Plasticicumulans*, in particular of the species *P. acidivorans*.

By supplying wastewater to step a), a mixture of activated sludge in wastewater is formed in the first reactor stage and the mixture is then subjected to reaction conditions accumulating the MSC during a first period of time to obtain activated sludge comprising the MSC in treated wastewater. The presence of dissolved oxygen is preferably achieved by supplying a molecular-oxygen-comprising gas, more preferably air to the first reactor. This may be done continuously or discontinuously, preferably continuously, during step a).

The amounts of RBCOD and of dissolved oxygen are such that they are not limiting for the production of the microbial storage compound. It will be appreciated that the minimum concentrations of RBCOD and dissolved oxygen will depend on the amount of micro-organisms capable of accumulating microbial storage compound present in the first reactor stage, the microbial storage compound to be produced and other process conditions such as temperature and pH of the mixture in the reactor.

The period of time applies to the average time the sludge stays in the first reactor stage before it is provided to the second reactor stage. In case of batch operation, the period of time applies to the mixture. If the wastewater or a sludge exchange recycle stream is intermittently or continuously added (and hence treated waste water is intermittently or continuously discharged), the period of time does not apply to the water but to the sludge itself, when the sludge is not or only partly discharged together with the (continuously) discharged treated wastewater.

The first period of time will end when a certain minimum concentration of RBCOD is achieved, when a certain amount of the MSC is produced, or when the oxygen consumption decreases. In a preferred embodiment with continuous operation in two reactors, the first period of time is normally predetermined by design reactor volume and wastewater flow. In this case the biomass concentration in the first reactor is controlled in order to achieve a certain minimum concentration of RBCOD or oxygen consumption rate. Alternatively, the RBCOD concentration in the mixture in the first reactor during step a) may be kept constant by adjusting the supply of the stream of wastewater or the concentration of biomass in the first reactor. The first period of time may then also end when the flow rate of wastewater supply drops below a certain value.

The level of RBCOD maintained in step a) is preferably at least 20 mg/l, more preferably at least 100 mg/l. The level of RBCOD maintained in step c) is preferably less than 100 mg/l, more preferably less than 40 mg/l, most preferably less than 20 mg/l. The loading rate of RBCOD in step a) may be between 2 and 80 kg/m$^3$·d, preferably between 4 and 40 kg/m$^3$·d.

At the end of step a) (first period of time), the MSC-loaded activated sludge comprises MSC (PHA) at a level of at least 50 wt. %, more preferably at least 60 wt. %, even more preferably at least 70 wt. % or even higher, based on dry weight of the organic part of the sludge.

The growth conditions applied in step c) comprise the presence of elements essential for growth at a sufficient, but limited level as described above, and allow uptake of the elements by the sludge. The growth conditions further comprise the presence of dissolved oxygen, as defined above.

At the end of step c) (second period of time), the grown activated sludge comprises residual MSC at a level of at least 20 wt. % based on dry weight of the organic part of the sludge, preferably at least 40 wt. %, more preferably at least 50 wt. %, and even more preferably at least 60 wt. %, on dry weight basis.

In an embodiment of the present process using a single reactor, the supply of waste water in step a) is reduced or interrupted during step c). Thus, the amount of RBCOD supplied during step c) and/or the average level of RBCOD present during step c) is lower, preferably least 50% lower than in step a). In a preferred arrangement, the supply of RBCOD is stopped during step c) (no RBCOD is added beyond what is already available to the sludge).

The first period of time (step a) and the second period of time (step c) correspond to the average times the sludge stays in these reactor stages before it is provided to the next stage in the cycle. In the event of using a single reactor, operated semi-continuously or batch-wise or pulse-wise, the first and second periods of time also correspond to the time between the start of the wastewater feed and nutrient feed (or sludge removal before nutrient feed), and between the start of nutrient feed and sludge removal or wastewater feed, respectively. The first period of time (step a) is preferably between 0.5 and 8 hours, more preferably between 1 and 4 hours. The second period of time (step c) is preferably between 0.1 and 6 h, more preferably between 0.2 and 4 h, even more preferably between 0.25 and 2 h. The second period of time can be relatively short when the up-take of nutrients is fast and a part of the growth can also be achieved in the subsequent step a). The total cycle can thus advantageously be between 0.5 h and 10 h, preferably between 1 and 6 h.

In steps b) and d) at least part of the sludge obtained in the preceding steps a) and c), respectively, is transferred, or if no physical transfer is needed, is caused to be present in the following steps c) and a) respectively. In step b) even the total sludge may be transferred to step c) provided that at least part of the sludge transferred in step d) is removed or harvested. In a preferred embodiment all sludge in step d) is transferred to step a) and at least part of the sludge transferred in step b) is removed or harvested.

Part of the MSC-loaded activated sludge produced in step a) can be removed from the cycle, and preferably harvested. Also, depending e.g. on the level of MSC after step c), a part of the grown activated sludge produced in step c) may be removed from the cycle and further processed and/or harvested. The amounts of sludge removed (and harvested), are preferably such that the average retention time of the sludge (SRT) in the system, the first and optional second reactor together, is less than 72 h, more preferably less than 48 h, yet more preferably less than 36 h, most preferably less than 24 h.

The part of the MSC-loaded activated sludge removed in step e) contains at least 50% of MSC (PHA), preferably at least 60%, more preferably at least 70% PHA, or even at least 75% based on dry weight of the organic part of the sludge, and the activated sludge caused to be present in a second reactor stage in step c) preferably contains at least 50% PHA. The part of the grown activated sludge optionally removed in step e) contains at least 20%, preferably at least 40%, more preferably at least 50%, even more preferably at least 60%, most preferably at least 65% MSC (PHA) based on dry weight of the organic part of the sludge. Most preferably, the MCS (in particular PHA) level of the MSC-loaded sludge (derived from step a)) and the level of grown activated sludge (derived from step c)) differs by less than 20%, most preferably less than 10% (of total dry weight of organic sludge). The difference in PHA content reached after the two reactor stages is mainly determined by the total sludge concentration applied in the two reactor stages and can be influenced by the amounts of sludge retained in and recycled between the first and second reactor stages and by the amounts of sludge removed in step e).

As indicated above, the reactor stages can have different forms. In a suitable embodiment, the first and second reactor stages are two separate reactors or two compartments of one reactor, and step a) is performed in the first reactor or compartment and step c) in the second reactor or compartment. The reactors are preferably operated in a continuous or semi-continuous mode or pulsing feed mode. In a continuous mode, the first reactor is continuously fed with wastewater and after the first period of time, in this case a certain retention time, wastewater with some or all of the sludge is transferred to the second reactor, where less wastewater or more dilute wastewater or preferably no RBCOD-containing wastewater at all is directly added, and elements essential for growth are fed as needed. MSC-loaded activated sludge can advantageously be separated from the wastewater between steps a) and c). In a semi-continuous mode or pulsing feed mode, wastewater is not added continuously, but e.g. pulse-wise. Nutrients for growth can also advantageously be supplied pulse-wise in step c) especially when a second reactor is used in a continuous system. As indicated above, this mode of operation is especially advantageous in the event that the level of Other Biodegradable COD (OBCOD) in the wastewater, as supplied to step a) is relatively high, in particular more than 0.2 times the level of RBCOD in step a).

Alternatively, the first and second reactor stages are stages in the same reactor, separated in space or, preferably, in time. Wastewater is then supplied in the first reactor stage, and the supply is preferably suppressed or interrupted during the second reactor stage c). Elements essential for growth are metered in step c) as needed, either continuously or pulse-wise. The single reactor can be operated preferably in a semi-continuous or pulse-wise mode. It is an advantage of the present invention that in step c) the wastewater flow does not always have to be interrupted, especially in case the RBCOD fraction of the biodegradable COD is high. In such a mode, step c) of relative promotion of growth, is initiated by supply of elements essential for growth within the limits as defined above. In another single-reactor embodiment, it can be operated in a Sequential Batch Reactor, comprising the sequence of filling with wastewater, reaction to allow accumulation, addition of nutrients, reaction to allow up-take of nutrients and limited growth, with settling of sludge, removal of effluent and partial removal of sludge either after accumulation (a) or after limited growth (c), or exceptionally both.

Thus, in one preferred embodiment involving one reactor, the present process comprises the following steps:

a) supplying a stream of the wastewater to the reactor and contacting the wastewater with the activated sludge under MSC-accumulating conditions during a first period of time to obtain MSC-loaded activated sludge comprising MSC preferably at a level of at least 60 wt. % based on dry weight of the organic part of the sludge, and treated wastewater;
b) optionally decreasing or interrupting the supply of wastewater during or after step a);
c) supplying elements essential for growth to the reactor, preferably pulse-wise, and contacting the wastewater with the activated sludge under growth conditions during a second period of time, wherein the supplied amount of at least one of said essential elements compared to the amount of RBCOD supplied in step a) limits the growth to an extent that not all MSC is used for growth, to obtain grown activated sludge comprising residual MSC, preferably at a level of at least 20 wt. % based on dry weight of the organic part of the sludge;
d) interrupting the supply of elements essential for growth during or after step c);
e) removing part of the treated wastewater from the reactor during or after step a) and/or during or after step c) and removing part of the MSC-loaded activated sludge during or after step a) and/or part of the grown activated sludge during or after step c), for example after step c) by settling in the reactor and discharging from the reactor, so that the average retention time of the activated sludge (SRT) in the reactor is less than 72 h, preferably less than 48 h;
and continuing with step a).

In another preferred embodiment, involving two reactors, or reactor compartments, the present process comprises the following steps:

a) supplying a stream of the wastewater to a first reactor and contacting the wastewater with the activated sludge under MSC-accumulating conditions during a first period of time, to obtain MSC-loaded activated sludge comprising MSC preferably at a level of at least 60 wt. % based on dry weight of the organic part of the sludge, and treated wastewater;
b) transferring at least part of the MSC-loaded activated sludge and at least part of the treated wastewater obtained in the first reactor to a second reactor;
c) supplying elements essential for growth to the second reactor and contacting the wastewater with the activated sludge under growth conditions during a second period of time, wherein the supplied amount of at least of one of said essential elements compared to the amount of RBCOD supplied in step a) limits the growth to an extent that not all MSC is used for growth, to obtain grown activated sludge comprising residual MSC preferably at a level of at least 20 wt. % based on dry weight of the organic part of the sludge;
d) transferring at least part of the grown activated sludge produced in the second reactor to the first reactor;
e) removing part of the treated wastewater from the first reactor during or after step a) and/or from the second reactor during or after step c) and removing part of the MSC-loaded activated sludge during or after step a) and/or part of the grown activated sludge during or after step c) so that the average retention time of the activated sludge (SRT) in the first and second reactor together is less than 72 h;
and continuing with step a).

In either embodiment, the amount of elements essential for growth supplied in step c) limiting the growth so that not all MSC (PHA) is used for growth, corresponds to $N_c/C_a$ or $P_n/C_a$ (or $S_n/C_a$, $K_n/C_a$, $Fe_n/C_a$ etc.) ratios as defined above. The process of the invention, in all embodiments, allows the production and isolation of microbial sludge having high levels of MSC, such as PHA. Thus, the MSC-containing activated sludge obtained in step e) comprises PHA at a level of at least 50 wt. %, preferably at least 60 wt. %, more preferably at least 70 wt. %, or in particular at least 75 wt. %, or even at least 80 wt. %, on the basis of dry organic sludge, which sludge can be separated and isolated.

The process of the invention can be preceded by a step of anaerobically fermenting the waste water to increase the level of RBCOD, in particular volatile fatty acids, and/or lactic acid and/or ethanol. Thus, the process may comprise a preceding step in which the raw wastewater is subjected to hydrolysis and/or fermentation in a separated reactor, for example an anaerobic reactor in which partial fermentation (hydrolysis, acidogenesis, acetogenesis) is achieved. Advantageously also during this step part of the nutrients present in the wastewater is removed thus lowering the nutrient to RBCOD ratio.

The sludge transfer from one reactor stage to the other and the removal of part of the sludge in step e) can be done by means known in the art, for example by means of sedimentation of sludge inside or outside the reactor or by means of a solid-liquid separator inside or outside the reactor. Suitable solid-liquid separators are known in the art and include settlers, hydro-cyclones, centrifuges, membranes and belt filters. When sludge retention is required, such separation can be carried out in a settler inside the first reactor, more preferably by means of sedimentation. For example, such sedimentation can be achieved by stopping the supply of wastewater and of air to the first reactor at the end of step a). Since the desired biomass accumulating storage compound is heavier than the undesired biomass, concentration of activated sludge before transfer of such sludge to the second reactor can advantageously be carried out such that undesired biomass is separated from the desired accumulating micro-organisms in the activated sludge to be transferred.

Part of the wastewater treated in step a) can be transferred to, or caused to be present in, in the event of the same physical reactor zone, the second reactor stage, typically with the (concentrated) mixture of sludge and treated wastewater, to serve as liquid reaction medium in growth step c). Alternatively, treated wastewater may be first separated from the solid sludge in an internal or external separator and then part of the separated treated wastewater may be transferred to the second reactor stage to serve as liquid reaction medium in step c).

Treated wastewater may be continuously withdrawn from the one or more reactors during steps a) through e) or batch-wise at the end of step a) and/or at the end of step c). In case treated wastewater is continuously withdrawn from the first reactor stage during steps a) through e), the reactor preferably comprises a settler for separating any sludge from the treated wastewater so that sludge is at least partly retained in the first reactor. Such settler may be located inside the reactor, preferably in an upper part of the reactor just before an outlet for treated wastewater, or outside the reactor with recycling of separated sludge to the first reactor. It will be appreciated that a settler for preventing sludge to be withdrawn from the first reactor with the continuous withdrawal of treated wastewater can be a different settler from a settler that may be used to concentrate activated sludge that is to be transferred to the second reactor stage in step b).

After removal of activated sludge after the first or second reactor stage, PHA may be recovered from this product stream in one or more further steps for application in for example bioplastics. Such steps are well-known in the art and typically comprise disruption of the microbial cells to harvest the microbial storage compound and further purification steps.

In step d), part of the grown activated sludge enriched in micro-organisms capable of accumulating the microbial storage compound is caused to be present in (or transferred to) the first reactor stage to form the activated sludge comprising micro-organisms capable of accumulating the microbial storage compound in step a).

The desired dissolved oxygen concentrations in steps a) and c) are maintained by supplying molecular oxygen or another oxygen-comprising oxidant to the first reactor or the second reactor during these steps, preferably by continuously feeding a stream of air to the relevant reactor.

The volume of the second reactor stage, if physically different from the first reactor stage, i.e. in the event of two reactors, is typically smaller than the volume of the first reactor stage. Preferably, the volume of the second reactor is from 10% to 90% of the volume of the first reactor, more preferably in the range of from 20% to 50% of the volume of the first reactor.

DESCRIPTION OF THE DRAWINGS

FIG. 1 schematically shows a one-reactor system according to the present invention. Accumulation and growth reactor 1 is provided with an air supply 2 with air distribution means. Wastewater containing RBCOD and limited in nutrients can be fed continuously or batch-wise through inlet line 3. Nutrients can be fed pulse-wise or batch-wise through inlet line 4. The reactor can be provided with sensors for measuring dissolved oxygen (DO), nutrients (e.g. nitrogen), (RB)COD, especially Volatile Fatty Acids (VFA), temperature, pH etc. The feed of RBCOD can be interrupted and nutrient can then be added when the RBCOD level in the reactor has dropped to a minimum level, e.g. 10 mg/l, as derived from the decreased oxygen consumption rate based on an increased DO concentration measured. Exit line 5 allows discharge of sludge-containing effluent. Effluent is separated in separator 6, from which clarified effluent is discharged through line 7. Alternatively, an internal settler can be provided in the reactor 1 (not shown). Sludge exits the separator through line 8 and is divided over optional return line 9 and discharge (product) line 10 in a controllable way. Optional exit line 11 allows to discharge sludge directly from the reactor 1. In a Sequential Batch Reactor system, sludge separation can be achieved in the reactor 1 by settling of the sludge after the air supply is temporary stopped and separator 6 can be dispensed with.

Figure 2:
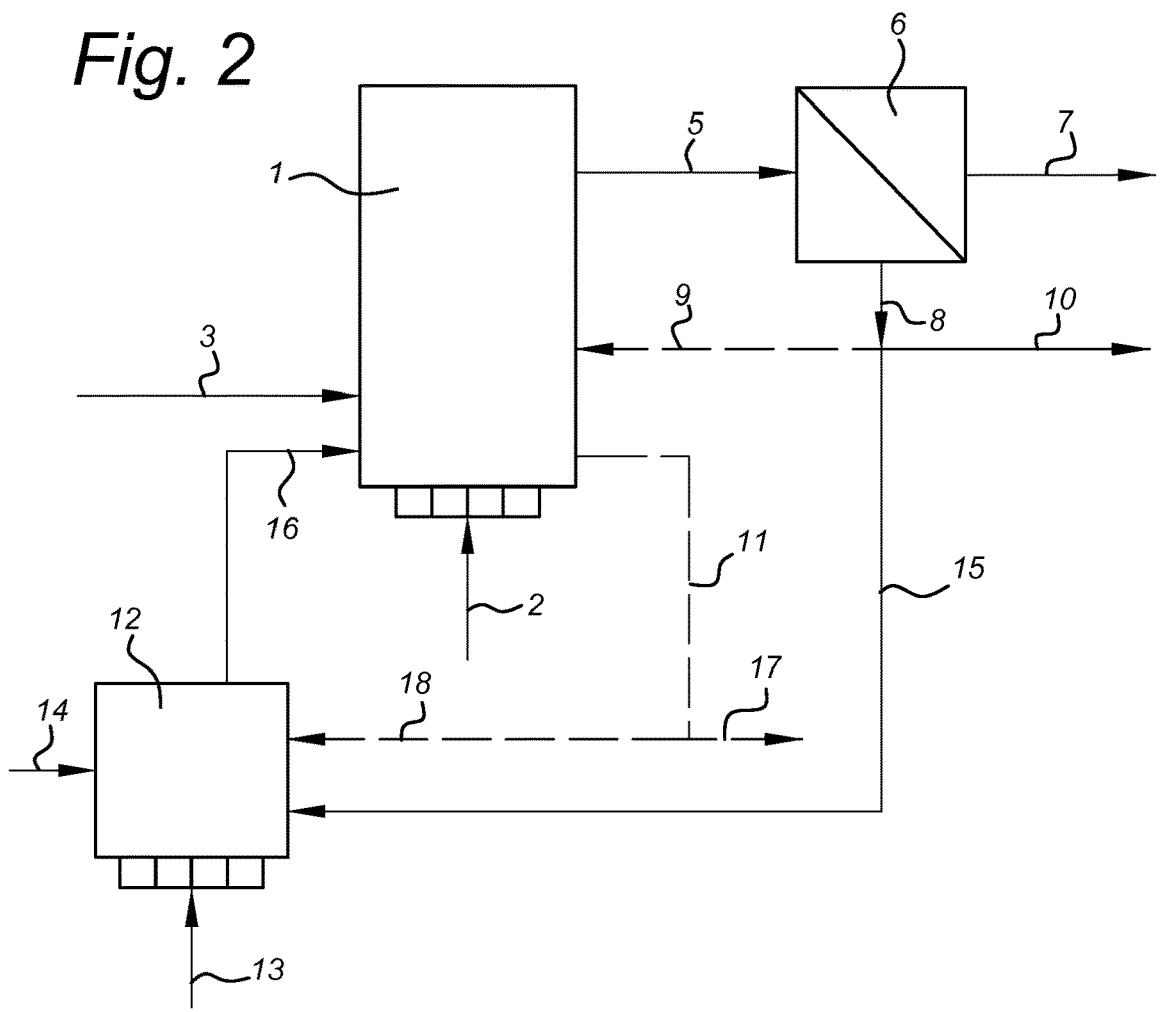

FIG. 2 schematically shows a two-reactor system according to the present invention. Accumulation reactor 1 is provided with an air supply 2 with air distribution means. Wastewater containing RBCOD and limited in nutrients can be fed continuously or semi-continuously through inlet line 3. Exit line 5 allows transfer of sludge-containing effluent to separator 6 (which also may be internal, not shown), from which clarified effluent is discharged through line 7. Sludge exits through line 8 and is divided over discharge (product) line 10, cycle line 15, and optional return line 9, in a controllable way. Line 15 carries sludge to growth reactor 12, which is provided with an air supply 13 with air distribution means. Nutrients can be fed to the growth reactor continuously or pulsed through inlet line 14. Optional exit line 11 allows to discharge sludge directly from the reactor 1 for removal or harvesting through exit line 17 and/or direct sludge feed to growth reactor 12 through line 18. Line 16 transfers the sludge containing effluent of reactor 12 back to reactor 1.

Figure 3:
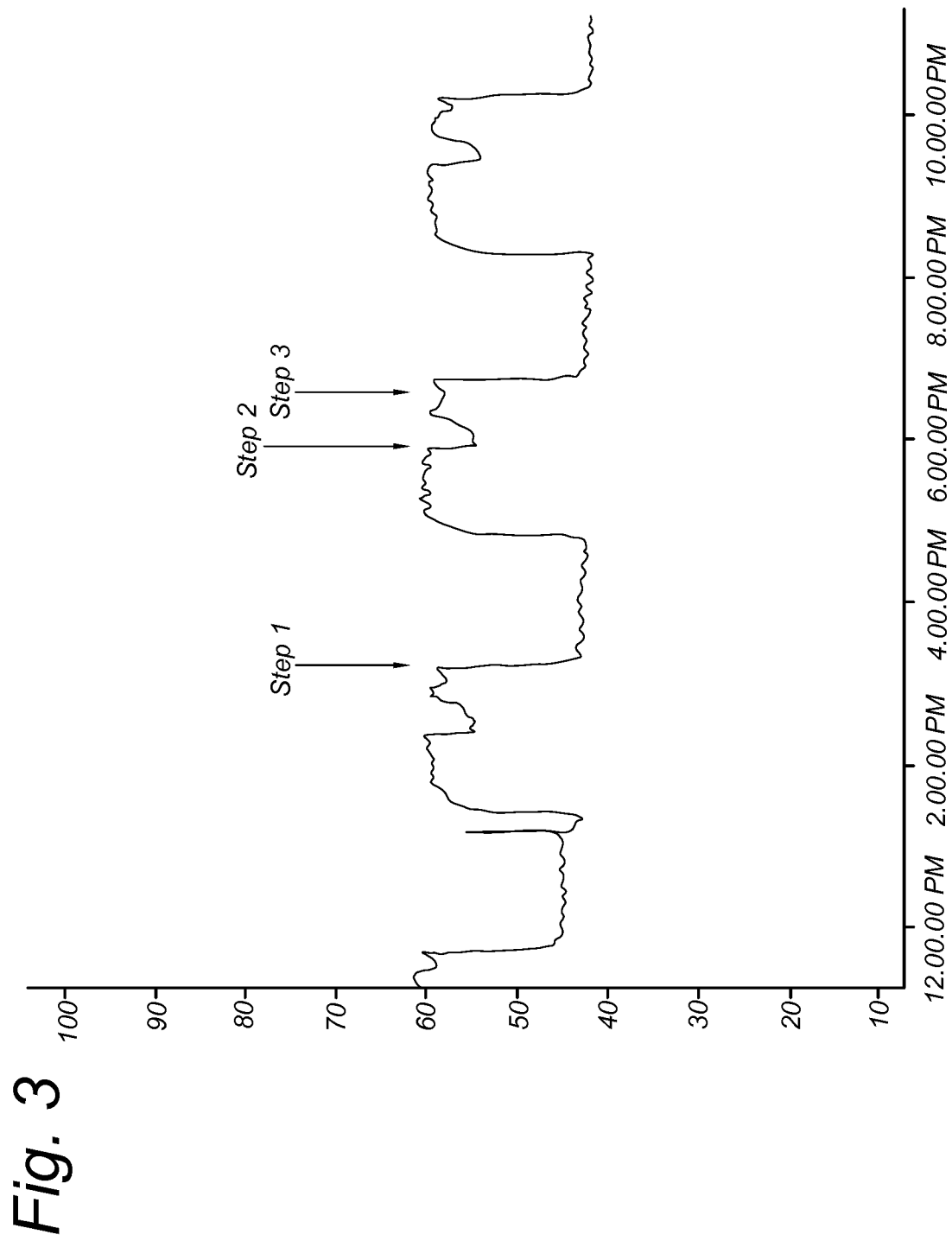
FIG. 3 shows dissolved oxygen during the process cycle.

FIG. 3 represents a graph showing dissolved oxygen (% saturation) during about three process cycles in a reactor operated as a SBR, as further described in Example 1. The graph shows the dissolved oxygen concentration as function of the addition of acetate (Step 1), acetate depletion, nutrient addition (Step 2) and partial removal of reactor content (Step 3).

Figure 4:
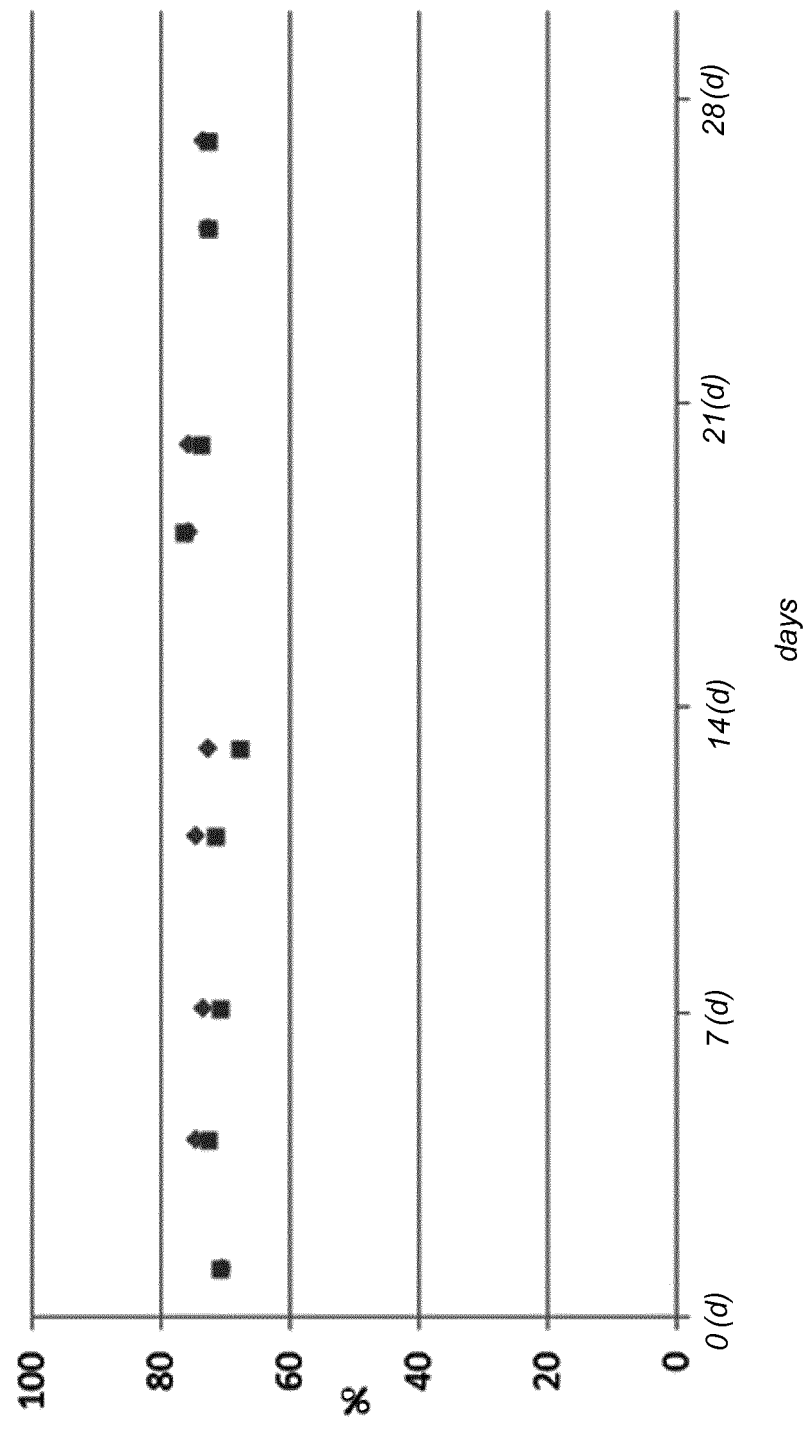
FIGS. 4 and 5 show PHA levels during the process in a one-reactor system and two-reactor system, respectively.

FIG. 4 shows PHA levels (% of dry organic matter) of the sludge during the process cycle in an SBR system. The diamonds (♦) show the PHA level at the end of the accumulation period and the squares (■) show the PHA level at the end of the growth period.

Figure 5:
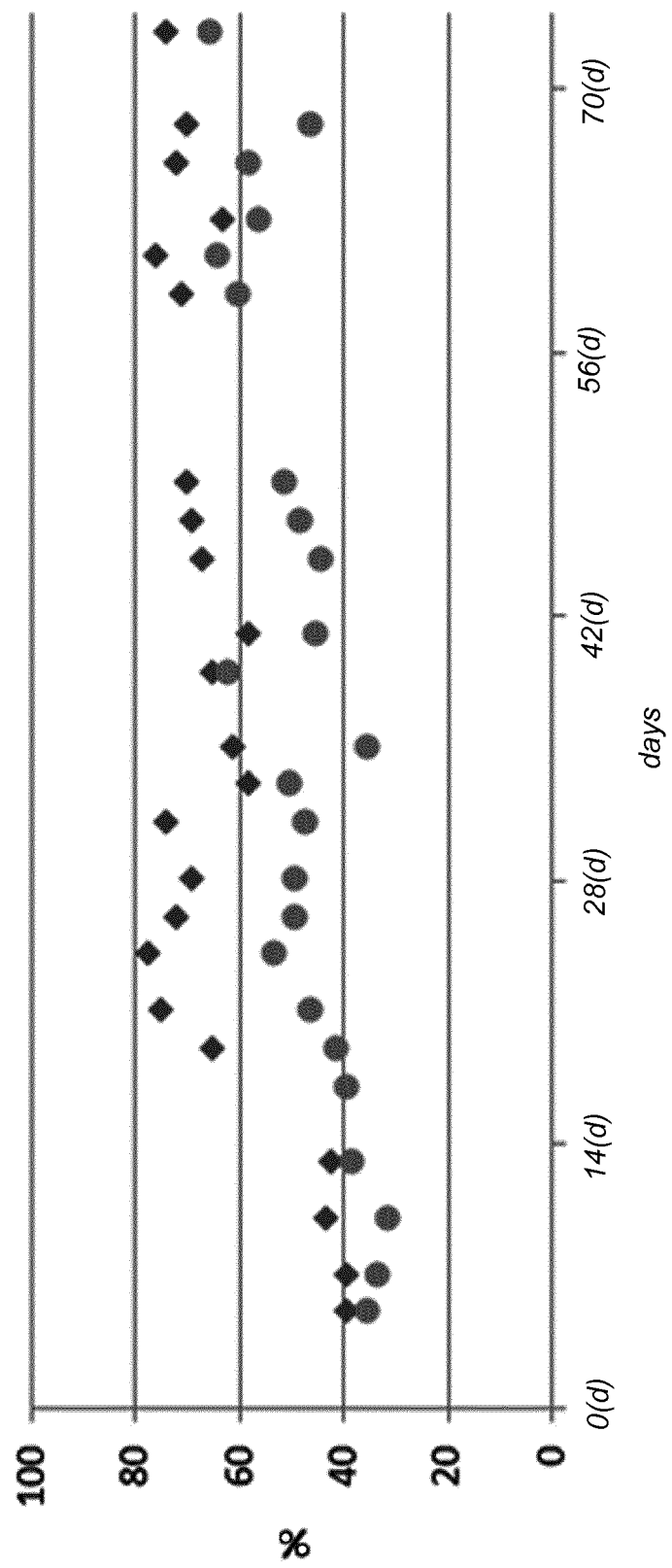

FIG. 5 shows PHA levels (% of dry organic matter) of the sludge during the process cycle in a continuously operated two-reactor system. The diamonds (♦) show the PHA level in the accumulation reactor and the spheres (•) show the PHA level in the growth reactor.

Example 1

A 6 litre double walled glass reactor was kept at 30° C.±1° C. The pH was kept between 6.8 and 7.0 by continuously adding a small amount of $CO_2$ gas. The reactor was operated as a Sequencing Batch Reactor with a cycle of 3.5 hours (210 minutes). Throughout the cycle the reactor was aerated with a fixed amount of air. The cycle consisted of:

Step 1 at t=0 minutes: Addition of 750 ml synthetic medium containing 10 g/l acetate (50% mol NaAc and 50% mol HAc), 200 mg/l K (as KCl), 100 mg/l Ca (as $CaCl_2$) and 50 mg/l Mg (as $MgCl_2$).

Step 2 at t=160 minutes: Addition of a commercial Nutrient mixture containing N (as urea), P (as $H_3PO_4$) and trace metals, where N is the limiting compound. Every cycle 90 mg/l of N is added.

Step 3 at t=200 minutes: Removal of 750 ml reactor content.
The system characteristics are as follows:
Hydraulic retention time (HRT): 28 hours
Average sludge retention time (SRT): 28 hours
First period of time: 160 minutes
Second period of time: 40 minutes
N/C in weight based on elements: 1/33)

When starting the reactor under the above conditions, the sludge already contained a mixture of PHA-accumulating organisms resulting from previous research. Initially the lab reactor was seeded with aerobic sludge from a municipal wastewater treatment plant.

FIG. 3 shows the measured dissolved oxygen concentration for about three cycles. It shows that as soon as acetate is fed to the reactor (Step 1) the dissolved oxygen concentration drops, indicating oxygen consumption required for acetate up-take and PHA production. After about 100 minutes the acetate is depleted and the dissolved oxygen concentration suddenly increases back to the base line level. As soon as nutrients are added (Step 2) the dissolved oxygen concentration decreases again and within 20 minutes the dissolved oxygen concentration increases back to the base line level, with a slight variation at removal of reactor content (Step 3). During the accumulation period (the low DO period after Step 1), the dissolved nitrogen concentration is low and the acetate concentration is depleted at the end of this period (not shown). During the nutrient up-take and limited growth period (after Step 2) the dissolved N concentration increases directly after nutrient addition and dropped again within the 20 minutes growth period.

The SBR reactor was operated for more than a month (which equals around 200 cycles or 25 times the sludge retention time (SRT)) at these settings and the PHA content was analysed at the end of the PHA accumulation period and at the end of the growth period. The PHA content in the sludge was determined by Thermogravimetric Analysis (TGA) in which the PHA content of the sludge samples is lost between 200 and 300° C. This results in a distinctive peak for weight loss based on which the PHA content can be determined. Results are shown FIG. 4.

FIG. 4 shows that the average PHA content in the sludge cycled between 70 and 78% wt based on organic content where the average PHA content after the PHA accumulation period is only slightly higher than the average PHA content after the growth period.

Example 2

A continuous set-up including two double walled glass reactors was operated for more than two months according to the flow sheet in FIG. 2 (with omission of lines 9, 11, 17 and 18) and under the following settings:

PHA accumulation reactor (1): 3.5 litre volume, temperature controlled at 30° C., pH controlled at pH 7.0 using an additional supply of carbon dioxide and aerated using air ensuring a dissolved oxygen concentration above 20% saturation.

Feed (3): 1.4 l/h synthetic medium containing 1.8 g/l acetate (50% mol NaAc and 50% mol HAc), 100 mg/l K (as KCl), 50 mg/l Ca (as $CaCl_2$) and 30 mg/l Mg (as $MgCl_2$)

Settler (6): 10 cm diameter with conical bottom

Growth reactor (12): 3 litre volume, temperature controlled at 30° C., pH controlled at pH 7.0 using an additional supply of carbon dioxide and aerated using air ensuring a dissolved oxygen concentration above 20% saturation. Pulse addition (14) every 30 minutes of a commercial Nutrient mixture containing N (as urea), P (as $H_3PO_4$) and trace metals, where N is the limiting compound. Every pulse 19 mg of N is added.

Sludge discharge (10) from settler: 0.4 l/h
Sludge recycle (15) from settler to the Growth reactor: 0.6 l/h.
The system characteristics are as follows:
First period of time equals the hydraulic retention time (HRT) in the PHA accumulation reactor: 1.8 hours
Second period of time equals the HRT in the Growth reactor: 5 hours
Average sludge retention time (SRT): around 17 hours
N/C in weight based on elements: 1/27
Organic loading rate of the first reactor: 17 $kg/m^3 \cdot d$ acetate.

When starting the system under the above conditions the reactors were seeded with sludge already containing a mixture of PHA-accumulating organisms taken from the reactor mentioned in Example 1. Initially the SBR lab reactor from example 1 was seeded with aerobic sludge from a municipal waste water treatment plant Under these conditions a steady state was achieved after a few weeks. It was confirmed by analysis that normally the acetate concentration in the PHA accumulation reactor and the settler overflow was between 50 and 100 mg/l. The dissolved oxygen concentration in the Growth reactor dropped directly after the pulse nutrient addition and increased again before the next pulse was supplied.

PHA content was analysed in samples taken from both the PHA accumulation reactor and the Growth reactor. Results are shown in FIG. 5. The average PHA content in the sludge in the PHA accumulation reactor was 70% by wt. based on organic content whereas the average PHA content in the Growth reactor was between 50 and 60% by wt.

The invention claimed is:

1. A cyclic process for producing a polyhydroxyalkanoate (PHA) from wastewater comprising Readily Biodegradable Chemical Oxygen Demand (RBCOD) using activated sludge comprising bacteria capable of accumulating PHA in the presence of elements essential for growth including nitrogen and phosphorus, the process comprising:
    (a) supplying a stream of the wastewater to a first reactor and contacting the wastewater with the activated sludge under PHA-accumulating conditions during a first period of time, the PHA-accumulating conditions comprising the presence of dissolved oxygen, wherein the wastewater supplied has a weight ratio of nitrogen to RBCOD-carbon on element basis (Na/Ca) of below 1/20, and/or a weight ratio of phosphorus to RBCOD-carbon on element basis (Pa/Ca) of below 1/100, to obtain PHA-loaded activated sludge comprising at least 60% PHA, based on dry weight of the organic part of the sludge, and treated wastewater;
    (b) transferring at least part of the PHA-loaded activated sludge and at least part of the treated wastewater from the first reactor to a second reactor;
    (c) supplying additional nitrogen and/or phosphorus to the second reactor and contacting the wastewater with the activated sludge under growth conditions during a second period of time, the growth conditions comprising the presence of dissolved oxygen, wherein the weight ratio, on element basis, of the amount of nitrogen or phosphorus supplied in step (c) together with any dissolved amount of nitrogen and phosphorus, respectively, supplied with the wastewater in step (a), to the amount of RBCOD-carbon supplied in step a) for nitrogen (Nc/Ca) is between 1/20 and 1/100, and for phosphorus (Pc/Ca) is between 1/100 and 1/500, to obtain grown activated sludge comprising residual PHA;
    (d) transferring at least part of the grown activated sludge produced in the second reactor to the first reactor to serve as the activated sludge of step (a) and repeating steps (a)-(d);
    (e) removing part of the treated wastewater from the first reactor during or after step (a) and/or from the second reactor during or after step (c) and removing part of the PHA-loaded activated sludge during or after step (a) and/or part of the grown activated sludge during or after step (c), wherein the activated sludge removed comprises PHA at a level of at least 60 wt. % based on dry weight of the organic part of the sludge, and wherein the removed parts are such that the average retention time of the activated sludge (SRT) in the first and second reactor together is less than 72 h.

2. The process according to claim 1, in which $N_c/C_a$ is between 1/20 and 1/75 and/or $P_c/C_a$ is between 1/100 and 1/375.

3. The process according to claim 1, in which in the wastewater supplied in step (a), the weight ratio of at least one element essential for growth to RBCOD-carbon is limited, the limiting ratio, on element basis, for nitrogen ($N_a/C_a$) being between 1/20 and 1/1000, and for phosphorus ($P_a/C_a$) being between 1/100 and 1/5000.

4. The process according to claim 3, in which the limiting ratio, on element basis, for $N_a/C_a$ is between 1/25 and 1/500 and/or for $P_a/C_a$ is between 1/125 and 1/2500.

5. The process according to claim 1, which is preceded by a step of lowering the weight ratio of N or P to RBCOD, by at least partially lowering the N or P concentration, and/or by adding RBCOD.

6. The process according to claim 1, in which the treated wastewater that is removed from the first and/or second reactor is separated from at least part of the activated sludge.

7. The process according to any claim 1, in which in step (e) part of the PHA-loaded activated sludge is removed during or after step (a) and the removed activated sludge removed comprises PHA at a level of at least 65 wt. %.

8. The process according to claim 1, in which the part of the PHA-loaded activated sludge and/or grown activated sludge removed in step (e) contains at least 70% PHA based on dry weight of the organic part of the sludge.

9. The process according to claim 8, in which the part of the PHA-loaded activated sludge and/or grown activated sludge removed in step (e) contains at least 80% PHA based on dry weight of the organic part of the sludge.

10. The process according to claim 1, in which the second reactor has a volume of between 10 and 90% of the volume of the first reactor and the reactors are operated in a continuous or semi-continuous mode or pulse-feed mode.

11. The process according to claim 1, in which in the wastewater supplied in step (a) the amount of Other Biodegradable COD (OBCOD) is more than 0.2 times the level of RBCOD in step (a).

12. The process according to claim 1, in which the level of RBCOD maintained in the first reactor stage in step (a) is at least 20 mg/l.

13. The process according to claim 1, in which the level of RBCOD maintained in the first reactor stage in step (a) is at least 100 mg/l.

14. The process according to claim 1, in which the first period of time is between 0.5 and 8 h, and the second period of time is between 0.1 and 6 h.

15. The process according to claim 14, in which the first period of time is between 1 and 4 h, and the second period of time is between 0.2 and 2 h.

16. The process according to claim 1, in which the bacteria comprise bacteria of the genus *Plasticicumulans*.

17. The process according to claim 16, in which the bacteria comprise bacteria of the species *P. acidivorans*.

18. The process according to claim 1, which is preceded by a step of anaerobically fermenting the waste water to increase the level of RBCOD.

19. The process according to claim 18, which is preceded by a step of anaerobically fermenting the waste water to increase the level of volatile fatty acids, medium-chain fatty acids, lactate, ethanol and/or MCFA.

20. The process according to claim 1, wherein the wastewater comprises RBCOD in the range of from 0.5 to 50 grams per liter.

* * * * *